United States Patent [19]

Klemann et al.

[11] 4,224,256
[45] Sep. 23, 1980

[54] METHOD OF PREPARING ETHER ADDUCTS OF ORGANIC-ALKALI METAL-BORON SALTS

[75] Inventors: Lawrence P. Klemann, Somerville; Eugene L. Stogryn, Edison, both of N.J.

[73] Assignee: Exxon Research & Engineering Co., Florham Park, N.J.

[21] Appl. No.: 34,578

[22] Filed: Apr. 30, 1979

[51] Int. Cl.² ............................................. C07F 5/02
[52] U.S. Cl. .................................. 568/6; 260/326.61; 260/340.6; 260/340.9 R; 260/345.1; 260/348.41; 549/4
[58] Field of Search ................... 260/606.5 B, 326.61, 260/340.6, 340.9 R, 345.1, 348.41; 549/4

[56] References Cited

U.S. PATENT DOCUMENTS

| | | | |
|---|---|---|---|
| 2,853,525 | 9/1958 | Wittig et al. | 260/606.5 B |
| 2,944,084 | 7/1960 | Blitzer et al. | 260/606.5 B |
| 3,055,944 | 9/1962 | Honeycutt | 260/606.5 B |
| 3,055,945 | 9/1962 | Honeycutt | 260/606.5 B |
| 3,311,662 | 3/1967 | Washburn et al. | 260/606.5 B |
| 4,134,923 | 1/1979 | Reimer | 260/606.5 B |

OTHER PUBLICATIONS

Chemical Abstracts 71 3416s (1969).
Angen. Chem. Int. Ed. Engl. 8 275 (1969).
Chemical Abstracts 72 139078m (1970).
Chemical Abstracts 53 936b (1959).
Chemical Abstracts 54 2671i (1960).
Kunze et al., J. Phys. Chem. 67 385 (1963).
Chemical Abstracts 79 83825c (1973).
Bhattacharyya et al., J. Phys. Chem. 69 608 (1965).
Chemical Abstracts 85 86471 (1976).
Chemical Abstracts 70 28974q (1969).
Wittig et al., Ann 563 110 (1949).
Chemical Abstracts 72 139078m (1970).
Chemical Abstracts 46 6607d (1952).

*Primary Examiner*—Helen M. S. Sneed
*Attorney, Agent, or Firm*—Kenneth P. Glynn

[57] ABSTRACT

The present invention is directed to a method of preparing an organic-alkali metal-boron salt of the formula:

$$ZBAr_mR_nAr'_x$$

wherein Z is an alkali metal selected from the group consisting of lithium and sodium, wherein B is boron, wherein Ar is an aromatic organic radical selected from a specified group of radicals, wherein R is an organic radical selected from methyl and ethyl, wherein Ar' is an aromatic organic radical selected from the group consisting of specified divalent dicyclic radicals, wherein m is a numerical value such that $0 \leq m \leq 4$, wherein n is a numerical value such that $0 \leq n \leq 2$, and wherein x is a numerical value such that $0 \leq x \leq 2$, subject to the provisio that the sum of m and n and x is such that the total valence of the organic radicals Ar, R and Ar' equals four. The method involves the reaction of a nitrogen-containing compound of the formula:

$$QHBAr_mR_nAr'_x$$

wherein Q is selected from the group consisting of specified nitrogen-containing groups, and wherein all other variables are as defined above, with an alkali metal compound of the formula:

$$ZX$$

wherein Z is defined above and wherein X is selected from the group consisting of hydrogen, specified nitrogen-containing radicals, any Ar as defined above and any R as defined above. The reaction is carried out in ether solvent such as dioxolane, dimethoxyethane, diglyme, tetrahydrofuran, tetrahydropyran, dioxane, diethyl ether and the like. In a preferred embodiment, Q is NH₃ and X is hydrogen.

9 Claims, No Drawings

METHOD OF PREPARING ETHER ADDUCTS OF ORGANIC-ALKALI METAL-BORON SALTS

BACKGROUND OF THE INVENTION

1. Field of the Invention

The present invention relates to a method of preparing high purity, anhydrous, ether adducts of alkali metal salts of the organic-alkali metal-boron type. More particularly, the present invention is directed to the method of preparing such compounds by reacting specified nitrogen-containing compounds with specified alkali metal-containing compounds, as more fully developed below.

2. Description of the Prior Art

There have been many techniques developed over the past few years for the synthesis of organic-alkali metal-boron salts. For example, Kunze et al, J. Phys. Chem. 67, 385 (1963) describe the preparation of lithium tetraphenyl boride by the reaction of sodium tetraphenyl boride with lithium chloride in ethanol and Bhattacharyya et al, J. Phys. Chem. 69, 608 (1965) describe the preparation of alkali metal tetraphenyl boride salts by the reaction of sodium tetraphenyl boride with lithium chloride in THF solvent. Revzin et al, Chemical Abstracts 70, 28974 q (1969) and Chemical Abstracts 71, 3416 s (1969) describe the preparation of lithium tetraphenyl boride from various salts, including ammonium tetraphenyl boride with lithium-containing ion exchange resins in acetone. Likewise, Kirgintsev et al, Chemical Abstracts 72, 139078 m (1970) describe the formation of lithium tetraphenyl borate and sodium tetraphenyl borate using potassium tetraphenyl borate with an ion exchange resin of the lithium form and using acetone solvent. Kozitskii, Chemical Abstracts 79, 83825 c (1973) describe the preparation of lithium tetraphenyl borate and the like by reaction of the potassium analogue with a lithium-containing ion exchange resin in the presence of acetone and water. (It should be noted that various prior art references refer to the same compounds as tetraphenyl borate or as tetraphenyl borides.) Khol'kin et al, Chemical Abstracts 85, 86471 u (1976) describe the preparation of lithium tetraphenyl boride from sodium tetraphenyl boride but do not describe the source of lithium except to point out that it is an exchange synthesis, i.e. exchange extraction synthesis. Wittig et al, Ann 563 110 (1949) and Chemical Abstracts 46, 6607 d (1952) respectively teach the preparation of lithium tetraphenyl boride and the like from triphenyl boron and trifluoro boron sources reacted with lithium phenyl salt in ether solvents. Grassberger et al, Angew. Chem. Int. Ed. Engl. 8, 275 (1969) describe the preparation of various alkali metal tetraorganyl borates by reaction of, for example, triphenyl boron with lithium tetraethyl boride without solvent.

Lee, Inorg. Chem., Volume 3, No. 2, Feb. 1964, pp. 289-90 describes the synthesis of lithium thiocyanate from hydrated lithium hydroxide and ammonium thiocyanate. Olah et al, Journal of the American Chemical Society, 97, No. 12, pp. 3559-3561 (1975) describe the synthesis of $LiO_2CCF_3$ from lithium hydride and $NH_4O_2CCF_3$. Morosi et al, Chemical Physics Letters, Vol. 47, No. 2, pp. 396-398 (1977) describe a theoretical analysis of a hypothetical reaction between the ammonium ion and lithium hydride in the gas phase to yield lithium salts. U.S. Pat. No. 3,049,406 describes the preparation of anhydrous lithium salts, including lithium halides, lithium pseudohalides, such as lithium cyanide and lithium thiocyanate, by the reaction of lithium hydride with halogens, cyanogen or thiocyanogen in an ether solution.

Notwithstanding all of the aforementioned prior art directed to various methods of preparing alkali metal salts, to date no reference has been published which teaches or renders obvious the method of preparation described herein.

BRIEF DESCRIPTION OF THE INVENTION

The present invention is directed to a method of preparing an ether adducts of organic-alkali metal-boron salt of the formula:

$$ZBAr_mR_nAr'_x \qquad (1)$$

wherein Z is an alkali metal selected from the group consisting of lithium and sodium, wherein B is boron, wherein Ar is an aromatic organic radical selected from a specified group of cyclic radicals, wherein R is an organic radical selected from methyl and ethyl, wherein Ar' is an aromatic organic radical selected from the group consisting of specified divalent dicyclic radicals, wherein m is a numerical value such that $0 \leq m \leq 4$, wherein n is a numerical value such that $0 \leq n \leq 2$, and wherein x is a numerical value such that $0 \leq x \leq 2$, subject to the proviso that the sum of m and n and x is such that the total valence of the organic radicals Ar, R and Ar' equals four.

The method involves the reaction of a nitrogen-containing compound of the formula:

$$QHBAr_mR_nAr'_x \qquad (2)$$

wherein Q is selected from the group consisting of specified nitrogen-containing groups, and wherein all other variables are as defined above, with an alkali metal compound of the formula: ZX Wherein Z is defined above and wherein X is selected from the group consisting of hydrogen, specified nitrogen containing radicals, any Ar as defined above and any R as defined above. The reaction is carried out in ether solvent.

DETAILED DESCRIPTION OF THE INVENTION

The present invention is directed to a method of preparing an ether adduct of organic-alkali metal-boron salt of the Formula (1) described above, namely:

$$ZBAr_mR_nAr'_x$$

wherein Z is an alkali metal selected from the group consisting of lithium and sodium, wherein B is boron, wherein Ar is an aromatic organic radical selected from the group consisting of $-C_6H_5$; $-C_6H_4-p-CH_3$; $-C_6H_4-p-F$; $-C_6H_4-m-F$; $-C_6H_4-p-CF_3$; $-C_6H_4-CF_3$; $-C_6H_4-o-CF_3$;

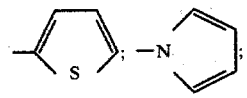

$-C_6F_5$, wherein R is an organic radical selected from the group consisting of $-CH_3$ and $-C_2H_5$, wherein Ar' is an aromatic organic radical selected from the group consisting of

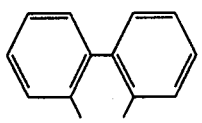

and

wherein m is a numerical value such that $0 \leq m \leq 4$, wherein x is a numerical value such that $0 \leq x \leq 2$ subject to the proviso that the sum of m and n and x is such that the total valence of the organic radicals Ar, R and Ar' equals four.

Included among the alkali metal salts which may be prepared by the present invention are:

$LiB(C_6H_5)_4$ $LiB(C_6H_4-p-F)_4$ $LiB(C_6H_4-p-CF_3)_4$ $LiB(C_6H_4-m-CF_3)_4$ $LiBCH_3(C_6H_5)_3$ $LiB(C_2H_5)_2(C_6H_4-p-F)_2$ $LiB(CH_3)_3C_6H_5$ $LiB(CH_3)(C_6F_5)$ 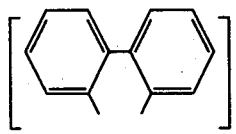

$LiB(CH_3)_2$ 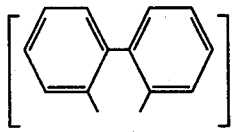

$LiB(C_6H_5)_2$ 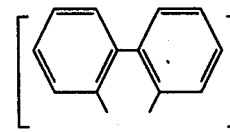

$LiB$ 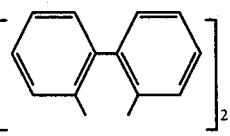

$LiB(C_6F_5)(C_6H_5)$ 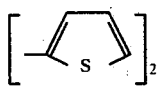

$LiB(CH_3)$ 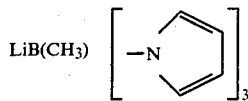

$LiB(C_6H_4-p-CF_3)_2$ 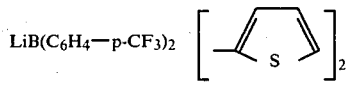

$LiB(C_2H_5)_2$ 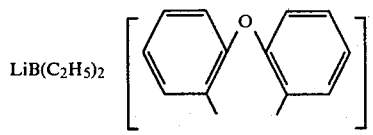

$LiB$ 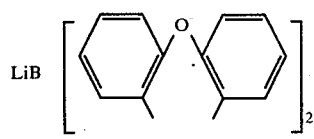

In addition to the foregoing specific salts, it is now seen that the generic formula above also encompasses the sodium analogues of the foregoing as well as various homologues and other similar compounds as included in Formula (1).

The method of the present invention involves reacting a nitrogen-containing compound of the formula:

$$QHBAr_mR_nAr_x' \qquad (2)$$

wherein Q is selected from the group consisting of $NH_3$; $HN(CH_3)_2$; $H_2NCH_3$; $N(C_2H_5)_3$; $HN(C_2H_5)_2$ and $H_2NC_2H_5$, and wherein all other variables are as defined above, with an alkali metal compound of the formula:

$$ZX \qquad (3)$$

wherein Z is as defined above and wherein X is selected from the group consisting of H; $NH_2$; $N(CH_3)_2$; $HNCH_3$; $N(C_2H_5)_2$; $HNC_2H_5$; $N(-CH(CH_3)_2)_2$; any Ar as defined above and any R as defined above, in ether solvent such as dioxolane, dimethoxyethane, diglyme, tetrahydrofuran, tetrahydropyran, dioxane, diethyl ether, etc.; as well as mixtures thereof.

Desirably, the variable Q in Formula (2) is selected from the group consisting of $NH_3$ and the mentioned tertiary amines, and is preferably $NH_3$. Also, desirably n in Formula (2) is zero or one and most desirably is equal to zero. Also, desirably, Ar is selected from the group consisting of $-C_6H_5$; $-C_6H_4-p-F$; $-C_6H_4-p-CH_3$; $-C_6H_4-p-CF_3$;

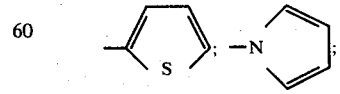

$-C_6H_4-m-F$; and $-C_6F_5$. Preferably, Ar is $-C_6H_5$. In the alkali metal compound of the formula:

$$ZX \qquad (3)$$

the variable Z is lithium or sodium and is preferably lithium. Also, the variable X is desirably hydrogen, $NH_2$; $N(CH_3)_2$ and $HNCH_3$. Preferably, the variable X is hydrogen or $NH_2$.

Among the cyclic and acyclic ether organic solvents which are useful in the present invention, dimethoxyethane, dioxolane, tetrahydrofuran, diethylether, tetrahydropyran and dioxane are desirable and dimethoxyethane, dioxolane and diethylether are preferred.

In performing the synthesis of the present invention the nitrogen-containing compound of Formula (2) is reacted with the alkali metal compound of Formula (3) in ratios so as to achieve a desirable amount of reaction product. Although it is not essential to the process, it is particularly advantageous to combine these two reactants so as to have a stoichiometric excess of the alkali metal compound of Formula (3). Concerning the solvents, it is desirable but not essential that adequate solvent be used so as to dissolve all of the desired reactant materials. In general, at least about 0.5 to about 50 milliliters of solvent per 1.0 gram of total reactants is useful. Preferably, at least about 2 to about 20 milliliters of solvent per 1.0 gram of total reactants may be used.

These reactions may be carried out at any operable pressure and temperature, and room temperature and pressure conditions will allow these reactions to readily occur in most instances. It may also be advantageous to pass an inert gas such as $N_2$, He, or Ar through or over the condensed reaction mixture so as to purge by-products including $H_2$ and volatile amines. In some instances, it is preferable to employ elevated temperatures, especially at reflux temperatures of the solvent-reactant systems. For example, reaction temperatures in the range of about 0° C. to about 175° C. may be used.

By the process of the present invention, significant advantages are achieved over prior art synthesis techniques. For example, by using the method of the present invention, anhydrous lithium salts may be obtained without requiring additional finishing steps to remove water. Also, the organic-alkali metal-boron salts produced may be used in situ in their solvent solution, or they may be isolated in solid form by conventional separation techniques. Further, using the ZX type reactant, the need to carefully control the stoichiometric ratio of the reactants is eliminated. Due to the very limited solubility of some of these ZX type reactants, excess may be used and only that which is stoichiometrically required by the reaction actually dissolves and is consumed. The presence of excess ZX serves as a gettering agent capable of removing from the solvent traces of water which are often considered undesirable for alkali metal salt solutions. This added benefit insures an anhydrous solution which may be useful directly in high purity applications, e.g. as electrolytes in alkali metal anode batteries.

The present invention is illustrated in detail by the following examples. However, these examples are presented for illustrative purposes only and the invention should not be construed to be limited thereto.

Example I

Twenty grams of sodium tetraphenylboride in 500 milliliters of distilled water were added to 470 milliliters of concentrated ammonium hydroxide with vigorous stirring. After 15 minutes, the solid was filtered and vacuum dried to yield approximately 17.2 grams of solid material (about 87%). The product, $NH_4B(C_6H_5)_4$, was then suspended in 80 milliliters of dioxolane containing about 1.6 grams of lithium hydride. This amount of lithium hydride constituted over 4 times the stoichiometric amount. This mixture was then heated and hydrogen and ammonia gases were evolved. After heating at reflux for about 4 hours, the mixture was allowed to cool and was filtered under a nitrogen blanket. The filtrate was then concentrated in a vacuum and then heated at atmospheric pressure and allowed to slowly cool. By this procedure, about 22.8 grams of clear, colorless crystals were obtained. Analysis of a dimethoxyethane solution of these crystals by NMR revealed that the crystals were a solvated composition of $(dioxolane)_4 LiB(C_6H_5)_4$. A lithium analysis showed about 1.06 percent lithium (theory, about 1.11%). The crystals contained about 0.022 wt% sodium. In order to confirm that the product obtained was anhydrous, a solution was prepared by dissolving 18.4 grams (approximately 29 mole) of the crystalline product and 5.5 grams of dimethoxyethane and about 15.1 grams of dioxolane. A Karl Fischer analysis was performed on the solution and showed that it contained less than 10 parts per million of water.

EXAMPLES 2–12

Solvated, anhydrous lithium borate salts of Examples 2–12 were prepared according to the method given in Example 1. The appropriate reactants, their quantities and the composition of the final lithium borate salt are presented in Table 1, below.

TABLE I $$QHBY_m + LiH \longrightarrow (Solvate)_z LiBy_m + QH + H_2$$

| Example | Q | Ar | m | g | LiH,g | Solvate*, mL | z | mp,°C. |
|---|---|---|---|---|---|---|---|---|
| 2 | $NH_3$ | p-$CF_3\phi$ | 4 | 45.2 | 2.94 | A,440 | 4 | 155–8 |
| 3 | $NH_3$ | p-$CF_3\phi$ | 4 | 86 | 4.5 | B,600 | 3 | 111–4 |
| 4 | $NH_3$ | p-$CF_3\phi$ | 4 | 72.1 | 4.73 | C,282 | 3 | 166–8 |
| 5 | $NH_3$ | m-$CF_3\phi$ | 4 | 77.5 | 3 | B,300 | 3 | 80–3 |
| 6 | $NH_3$ | m-$CF_3\phi$ | 4 | 104.4 | 6.9 | C,500 | 3 | 111–2 |
| 7 | $(CH_3)_3N$ | p-$F\phi$ | 4 | 16 | 1.8 | A,100 | 4 | 128–31 |
| 8 | $NH_3$ | p-$F\phi$ | 4 | 250 | 24 | A,900 | 4 | 128–31 |
| 9 | $NH_3$ | p-$F\phi$ | 4 | 125 | 12 | C,400 | 3 | 111–2 |
| 10 | $NH_3$ | 2-Thienyl | 4 | 72.2 | 6.4 | C,250 | 3 | 96–98 |
| 11 | $(CH_3)_3N$ | 2-Thienyl | 4 | 35 | 3.42 | A,500 | 4 | 140–5 |

TABLE I-continued $$QHBY_m + LiH \longrightarrow (Solvate)_zLiBy_m + QH + H_2$$

| Example | Q | Ar | m | g | LiH,g | Solvate*, mL | z | mp,°C. |
|---------|---|-----|---|-----|-------|--------------|---|--------|
| 12 | (CH$_3$)$_3$N | 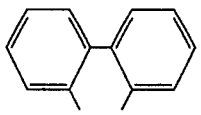 | 2 | 5.4 | 0.58 | A,60 | 4 | — |

*Legend:
A = Dioxolyne
B = Diethyl ether
C = Dimethoxyethand

EXAMPLE 13

NH$_4$B(C$_6$H$_5$)$_4$(114 g, 0.34 mole) and 600 mL of dimethoxyethane (distilled from Na, benzophenone) were combined in a 1000 ml flask containing a magnetic stirrer bar and fitted with a thermometer, reflux condenser and nitrogen inlet. A glass adapter, attached by a short length of Gooch tubing to a 125 mL Erlenmeyer flask (containing 10 g, 1.3 mole, LiH) is fitted to the flask and the solid LiH is added with vigorous stirring over 20 minutes. During this addition, gas (H$_2$ and NH$_3$) is evolved through a bubbler in the nitrogen line and the temperature of the reaction mixture rises to about 45° C. After this addition is complete, the mixture is warmed to achieve reflux for four hours. The mixture is then cooled, filtered to remove excess LiH, and the filtrate is concentrated to about 275 mL on a vacuum rotary evaporator. The concentrated solution is warmed to about 80° C. and is transferred to a glass-stoppered Erlenmeyer flask. Cooling of this solution to about −20° C. results in crystallization of the product which is isolated by filtration and dried to afford 175 g (86% yield) of (dimethoxyethane)$_3$LiB(C$_6$H$_5$)$_4$ as white crystals. The ratio of dimethoxyethane to anion is established by proton nmr of the product dissolved in dioxolane, and by elemental analysis:

Calculated for (dimethoxyethane)$_3$LiB(C$_6$H$_5$)$_4$, MW 596.556:

C 72.48%, H 8.45%, Li 1.16%; Found: C 72.57%, H 8.38%, Li 1.10%.

EXAMPLE 14

To a 100 mL flask, fitted with a magnetic stirring bar, reflux condenser, N$_2$ inlet, and dropping funnel were charged 6.74 g (20 mole) NH$_4$B(C$_6$H$_5$)$_4$ and 50 mL of diethyl ether. Under N$_2$ and with cooling to −50° C. a solution of phenyllithium (12 mL, 1.7 M in ether-benzene) was added dropwise over 10 minutes. The slurry was allowed to warm to room temperature and then was heated at reflux for about 10 hours. The mixture was cooled, filtered and the solid residue was dissolved in a minimum amount of warm dioxolane. About 0.6 g of insoluble material (probably unreacted NH$_4$B(C$_6$H$_5$)$_4$) was removed by filtration. Upon cooling the dioxolane solution to about 0° C., white crystals were deposited. The crystals (1.5 g) were isolated and addition of pentane to remaining dioxolane solution produced an additional 8.8 g of product.

The product was characterized by nmr (~4/1 ratio of dioxolane/B(C$_6$H$_5$)$_4$—), and by elemental analysis. Calculated for (dioxolane)$_4$LiB(C$_6$H$_5$)$_4$, MW 622.508: C 69.46%, H 7.12%, N ~0%. Found: C 69.41%, H 7.01%, N 0.59%.

The trace of nitrogen in the product is believed to be due to LiNH$_2$(about 1%) formed by a side reaction between phenyllithium and ammonia. The total yield of product was 10.3 g or 91% of theory for (dioxolane)$_4$·LiB(C$_6$H$_5$)$_4$. This example demonstrated that phenyllithium can be used to deprotonate NH$_4$+ion and thereby form LiB(C$_6$H$_5$)$_4$ from NH$_4$B(C$_6$H$_5$)$_4$.

What is claimed is:

1. A method of preparing an ether adduct of alkali metal salt of the formula:

$$ZBAr_mR_nAr_x'$$

wherein Z is an alkali metal selected from the group consisting of Li and Na, wherein B is boron, wherein Ar is an organic radical selected from the group consisting of —C$_6$H$_5$; C$_6$H$_4$—p—CH$_3$; —C$_6$H$_4$—p—F; —C$_6$H$_4$—m—F; —C$_6$H$_4$—p—CF$_3$; —C$_6$H$_4$—m—CF$_3$; —C$_6$H$_4$—o—CF$_3$;

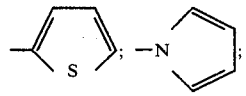

—C$_6$F$_5$, wherein R is an organic radical selected from the group consisting of —CH$_3$ and —C$_2$H$_5$ wherein Ar' is an organic radical selected from the group consisting of

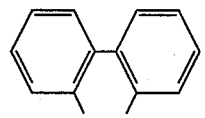

and

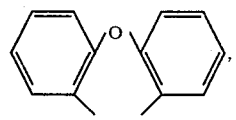

wherein m is a numerical value such that 0≦m≦4, wherein n is a numerical value such that 0≦n≦2, and wherein x is a numerical value such that 0≦x≦2, subject to the proviso that the sum of m and n and x is such that the total valence of the organic radicals Ar, R and Ar' equals four, comprising:

reacting a nitrogen-containing compound of the formula:

$$QHBAr_mR_nAr_x'$$

wherein Q is selected from the group consisting of NH$_3$; N(CH$_3$)$_3$, HN(CH$_3$)$_2$; H$_2$NCH$_3$; N(C$_2$H$_5$)$_3$; HN(C$_2$H$_5$)$_2$ and H$_2$NC$_2$H$_5$ and wherein all other variables are as defined above, with an alkali metal compound of the formula:

ZX wherein Z is as defined above and wherein X is selected from the group consisting of H; NH$_2$; N(CH$_3$)$_2$; HNCH$_3$; N(C$_2$H$_5$)$_2$; HNC$_2$H$_5$; N(—CH(CH$_3$)$_2$)$_2$; any Ar as defined above and any R as defined above, in ether solvent.

2. The method of claim 1 wherein said variable Ar is selected from the group consisting of —C$_6$H$_5$; —C$_6$H$_4$—p—F; —C$_6$H$_4$—p—CF$_3$; —C$_6$H$_4$—p—CH$_3$;

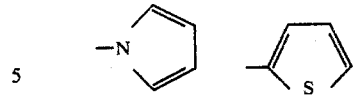

—C$_6$H$_4$—m—F and —C$_6$F$_5$.

3. The method of claim 2 wherein n is zero.

4. The method of claim 3 wherein X is selected from the group consisting of H; NH$_2$; N(CH$_3$)$_2$ and HNCH$_3$.

5. The method of claim 4 wherein said solvent is selected from the group consisting of dioxolane, dimethoxyethane, diglyme, tetrahydrofuran, tetrahydropyran dioxane, diethyl ether and mixtures thereof.

6. The method of claim 4 wherein a stoichiometric excess of the alkali metal compound ZX is used.

7. The method of claim 1,2,3,4,5 or 6 wherein the alkali metal Z is lithium.

8. The method of claim 1,2,3,4,5 or 6 wherein said solvent is selected from the group consisting of dimethoxyethane, dioxolane and diethyl ether.

9. The method of claim 1,2,3,4,5 or 6 wherein X is selected from the group consisting of H and NH$_2$.

\* \* \* \* \*